(12) United States Patent
Ortiz et al.

(10) Patent No.: US 8,317,074 B2
(45) Date of Patent: *Nov. 27, 2012

(54) ELECTROACTIVE POLYMER-BASED ARTICULATION MECHANISM FOR CIRCULAR STAPLER

(75) Inventors: Mark Ortiz, Milford, OH (US); Frederick Shelton, IV, Hillsboro, OH (US); Joseph Hueil, Loveland, OH (US); Jeffrey Swayze, Hamilton, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1530 days.

This patent is subject to a terminal disclaimer.

(21) Appl. No.: 11/162,989

(22) Filed: Sep. 30, 2005

(65) Prior Publication Data

US 2006/0047307 A1 Mar. 2, 2006

Related U.S. Application Data

(63) Continuation-in-part of application No. 11/082,495, filed on Mar. 17, 2005, now Pat. No. 7,506,790.

(60) Provisional application No. 60/591,694, filed on Jul. 28, 2004.

(51) Int. Cl.
*A61B 17/068* (2006.01)

(52) U.S. Cl. ............ 227/176.1; 227/175.1; 227/180.1; 606/139; 606/219

(58) Field of Classification Search .... 227/175.1–182.1; 606/139, 219; 604/95.01, 95.04, 95.05; 600/114
See application file for complete search history.

(56) References Cited

U.S. PATENT DOCUMENTS

| | | | |
|---|---|---|---|
| 2,711,461 A | | 6/1955 | Happe |
| 4,473,077 A | * | 9/1984 | Noiles et al. ............... 227/179.1 |
| 4,543,090 A | * | 9/1985 | McCoy ...................... 604/95.05 |
| 4,554,064 A | | 11/1985 | McClintock et al. |
| 4,566,620 A | | 1/1986 | Green et al. |
| 4,601,705 A | * | 7/1986 | McCoy ...................... 604/95.05 |
| 4,753,223 A | * | 6/1988 | Bremer ........................ 600/140 |
| 4,892,545 A | | 1/1990 | Day et al. |
| 5,031,814 A | | 7/1991 | Tompkins et al. |
| 5,040,715 A | | 8/1991 | Green et al. |
| 5,071,052 A | | 12/1991 | Rodak et al. |
| 5,137,198 A | | 8/1992 | Nobis et al. |
| 5,171,249 A | | 12/1992 | Stefanchik et al. |
| 5,202,914 A | | 4/1993 | Kim et al. |

(Continued)

FOREIGN PATENT DOCUMENTS

DE 4015562 A1 11/1991

(Continued)

OTHER PUBLICATIONS

Dec. 5, 2008 Office Action for U.S. Appl. No. 11/162,991.

(Continued)

*Primary Examiner* — Darwin Erezo

(57) ABSTRACT

Methods and devices are provided for actuating and/or articulating a circular stapler. In one exemplary embodiment, a circular stapler is provided having an elongate shaft with a stapling apparatus coupled thereto. An electrically expandable and contractible actuator, such as an electroactive polymer actuator, can be used to pivotally or angularly adjust a position of the stapling apparatus relative to the elongate shaft by delivering energy to the electroactive polymer actuator. In another embodiment, an electroactive polymer actuator can be used to actuate the stapling apparatus, thereby driving one or more staples, preferably in a substantially curved pattern, into tissue. The actuator can alternatively or additionally drive a blade distally to cut tissue being stapled.

7 Claims, 13 Drawing Sheets

U.S. PATENT DOCUMENTS

| | | | |
|---|---|---|---|
| 5,263,629 A | 11/1993 | Trumbull et al. | |
| 5,290,240 A | 3/1994 | Horres, Jr. | |
| 5,312,023 A | 5/1994 | Green et al. | |
| 5,330,087 A | 7/1994 | Murray et al. | |
| 5,372,124 A | 12/1994 | Takayama et al. | |
| 5,387,194 A | 2/1995 | Williams et al. | |
| 5,389,098 A | 2/1995 | Tsuruta et al. | |
| 5,397,046 A | 3/1995 | Savage et al. | |
| 5,397,324 A | 3/1995 | Carroll et al. | |
| 5,399,256 A | 3/1995 | Bohs et al. | |
| 5,403,312 A | 4/1995 | Yates et al. | |
| 5,413,267 A | 5/1995 | Solyntjes et al. | |
| 5,413,268 A | 5/1995 | Green et al. | |
| 5,431,668 A | 7/1995 | Burbank, III et al. | |
| 5,441,193 A | 8/1995 | Gravener | |
| 5,445,304 A | 8/1995 | Plyley et al. | |
| 5,465,895 A | 11/1995 | Knodel et al. | |
| 5,468,250 A | 11/1995 | Paraschac et al. | |
| 5,484,095 A | 1/1996 | Green et al. | |
| 5,503,638 A | 4/1996 | Cooper et al. | |
| 5,520,787 A | 5/1996 | Hanagan et al. | |
| 5,535,937 A | 7/1996 | Boiarski et al. | |
| 5,542,594 A | 8/1996 | McKean et al. | |
| 5,549,628 A | 8/1996 | Cooper et al. | |
| 5,555,555 A | 9/1996 | Sato et al. | |
| 5,562,239 A | 10/1996 | Boiarski et al. | |
| 5,584,425 A | 12/1996 | Savage et al. | |
| 5,592,668 A | 1/1997 | Harding et al. | |
| 5,599,329 A | 2/1997 | Gabbay | |
| 5,601,582 A | 2/1997 | Shelton et al. | |
| 5,609,285 A | 3/1997 | Grant et al. | |
| 5,624,452 A | 4/1997 | Yates | |
| 5,634,584 A | 6/1997 | Okorocha et al. | |
| 5,653,721 A | 8/1997 | Knodel et al. | |
| 5,661,887 A | 9/1997 | Byrne et al. | |
| 5,665,285 A | 9/1997 | Hattori et al. | |
| 5,667,517 A | 9/1997 | Hooven | |
| 5,669,918 A | 9/1997 | Balazs et al. | |
| 5,673,840 A | 10/1997 | Schulze et al. | |
| 5,673,841 A | 10/1997 | Schulze et al. | |
| 5,680,983 A | 10/1997 | Plyley et al. | |
| 5,688,270 A | 11/1997 | Yates et al. | |
| 5,692,668 A | 12/1997 | Schulze et al. | |
| 5,693,042 A | 12/1997 | Boiarski et al. | |
| 5,702,409 A | 12/1997 | Rayburn et al. | |
| 5,704,534 A | 1/1998 | Huitema et al. | |
| 5,709,334 A | 1/1998 | Sorrentino et al. | |
| 5,735,445 A | 4/1998 | Vidal et al. | |
| 5,769,892 A | 6/1998 | Kingwell | |
| 5,779,130 A | 7/1998 | Alesi et al. | |
| 5,792,165 A | 8/1998 | Klieman et al. | |
| 5,797,537 A | 8/1998 | Oberlin et al. | |
| 5,810,855 A | 9/1998 | Rayburn et al. | |
| 5,826,776 A | 10/1998 | Schulze et al. | |
| 5,829,662 A | 11/1998 | Allen et al. | |
| 5,855,565 A | 1/1999 | Bar-Cohen et al. | |
| 5,865,361 A | 2/1999 | Milliman et al. | |
| 5,868,744 A | 2/1999 | Willmen | |
| 5,876,401 A | 3/1999 | Schulze et al. | |
| 5,901,895 A | 5/1999 | Heaton et al. | |
| 5,902,312 A | 5/1999 | Frater et al. | |
| 5,908,427 A | 6/1999 | McKean et al. | |
| 5,918,791 A | 7/1999 | Sorrentino et al. | |
| 5,959,852 A | 9/1999 | Deloy et al. | |
| 5,964,774 A | 10/1999 | McKean et al. | |
| 5,972,165 A | 10/1999 | Sethna et al. | |
| 6,010,054 A | 1/2000 | Johnson et al. | |
| 6,032,849 A | 3/2000 | Mastri et al. | |
| 6,033,427 A | 3/2000 | Lee | |
| 6,063,097 A | 5/2000 | Oi et al. | |
| 6,079,606 A | 6/2000 | Milliman et al. | |
| 6,109,500 A | 8/2000 | Alli et al. | |
| 6,202,914 B1 | 3/2001 | Geiste et al. | |
| 6,241,139 B1 | 6/2001 | Milliman et al. | |
| 6,302,311 B1 | 10/2001 | Adams et al. | |
| 6,330,965 B1 | 12/2001 | Milliman et al. | |
| 6,488,197 B1 | 12/2002 | Whitman | |
| 6,494,896 B1 | 12/2002 | D'Alessio et al. | |
| 6,503,257 B2 | 1/2003 | Grant et al. | |
| 6,503,259 B2 | 1/2003 | Huxel et al. | |
| 6,514,237 B1 | 2/2003 | Maseda | |
| 6,545,384 B1 | 4/2003 | Pelrine et al. | |
| 6,577,899 B2 | 6/2003 | Lebel et al. | |
| 6,583,533 B2 | 6/2003 | Pelrine et al. | |
| 6,586,859 B2 | 7/2003 | Kornbluh et al. | |
| 6,595,852 B2 | 7/2003 | Wang | |
| 6,652,521 B2 | 11/2003 | Schulze | |
| 6,656,193 B2 | 12/2003 | Grant et al. | |
| 6,667,825 B2 | 12/2003 | Lu et al. | |
| 6,669,073 B2 | 12/2003 | Milliman et al. | |
| 6,699,245 B2 | 3/2004 | Dinger et al. | |
| 6,716,233 B1 | 4/2004 | Whitman | |
| 6,740,079 B1 | 5/2004 | Eggers et al. | |
| 6,770,027 B2 * | 8/2004 | Banik et al. | 600/146 |
| 6,786,382 B1 | 9/2004 | Hoffman | |
| 6,830,174 B2 | 12/2004 | Hillstead et al. | |
| 6,835,173 B2 | 12/2004 | Couvillon, Jr. | |
| 6,840,246 B2 | 1/2005 | Downing | |
| 6,905,057 B2 | 6/2005 | Swayze et al. | |
| 6,913,579 B2 | 7/2005 | Truckai et al. | |
| 6,923,804 B2 | 8/2005 | Eggers et al. | |
| 6,959,852 B2 | 11/2005 | Shelton, IV et al. | |
| 6,964,363 B2 | 11/2005 | Wales et al. | |
| 6,969,395 B2 | 11/2005 | Eskuri | |
| 6,978,921 B2 | 12/2005 | Shelton, IV et al. | |
| 6,981,628 B2 | 1/2006 | Wales | |
| 6,988,649 B2 | 1/2006 | Shelton, IV et al. | |
| 7,000,818 B2 | 2/2006 | Shelton, IV et al. | |
| 7,000,819 B2 | 2/2006 | Swayze et al. | |
| 7,044,352 B2 | 5/2006 | Shelton, IV et al. | |
| 7,055,731 B2 | 6/2006 | Shelton, IV et al. | |
| 7,063,699 B2 | 6/2006 | Hess et al. | |
| 7,074,217 B2 | 7/2006 | Strul et al. | |
| 7,083,075 B2 | 8/2006 | Swayze et al. | |
| 7,111,769 B2 | 9/2006 | Wales et al. | |
| 7,140,528 B2 | 11/2006 | Shelton, IV | |
| 7,143,925 B2 | 12/2006 | Shelton, IV et al. | |
| 7,143,926 B2 | 12/2006 | Shelton, IV et al. | |
| 7,147,138 B2 | 12/2006 | Shelton, IV | |
| 7,208,005 B2 | 4/2007 | Frecker et al. | |
| 7,213,736 B2 * | 5/2007 | Wales et al. | 227/180.1 |
| 7,238,195 B2 | 7/2007 | Viola | |
| 7,320,700 B2 | 1/2008 | Cooper et al. | |
| 7,338,509 B2 | 3/2008 | Mattison | |
| 7,354,447 B2 | 4/2008 | Shelton, IV et al. | |
| 7,364,061 B2 | 4/2008 | Swayze et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,509 B2 * | 7/2008 | Ortiz et al. | 227/176.1 |
| 7,407,074 B2 * | 8/2008 | Ortiz et al. | 227/175.1 |
| 7,431,730 B2 | 10/2008 | Viola | |
| 7,487,899 B2 | 2/2009 | Shelton, IV et al. | |
| 7,506,790 B2 * | 3/2009 | Shelton, IV | 227/176.1 |
| 7,513,408 B2 | 4/2009 | Shelton, IV et al. | |
| 7,517,356 B2 | 4/2009 | Heinrich | |
| 7,559,452 B2 | 7/2009 | Wales et al. | |
| 7,607,557 B2 | 10/2009 | Shelton, IV et al. | |
| 7,641,093 B2 | 1/2010 | Doll et al. | |
| 7,862,579 B2 * | 1/2011 | Ortiz et al. | 606/205 |
| 7,879,070 B2 * | 2/2011 | Ortiz et al. | 606/205 |
| 7,914,551 B2 * | 3/2011 | Ortiz et al. | 606/205 |
| 2001/0029384 A1 | 10/2001 | Nicholas et al. | |
| 2002/0074005 A1 | 6/2002 | Hogg et al. | |
| 2002/0108112 A1 | 8/2002 | Wallace et al. | |
| 2002/0165541 A1 | 11/2002 | Whitman | |
| 2003/0065358 A1 | 4/2003 | Frecker et al. | |
| 2003/0069474 A1 | 4/2003 | Couvillon | |
| 2003/0199870 A1 | 10/2003 | Truckai et al. | |
| 2003/0207606 A1 | 11/2003 | Ho | |
| 2003/0236531 A1 | 12/2003 | Couvillon | |
| 2004/0002726 A1 | 1/2004 | Nunez et al. | |
| 2004/0050971 A1 | 3/2004 | Rueger et al. | |
| 2004/0054322 A1 | 3/2004 | Vargas | |
| 2004/0068224 A1 | 4/2004 | Couvillon et al. | |
| 2004/0097971 A1 | 5/2004 | Hughett | |
| 2004/0138700 A1 | 7/2004 | Cooper et al. | |

| | | | |
|---|---|---|---|
| 2004/0149802 | A1 | 8/2004 | Whitman |
| 2004/0232195 | A1 | 11/2004 | Shelton et al. |
| 2004/0232196 | A1 | 11/2004 | Shelton et al. |
| 2004/0232197 | A1 | 11/2004 | Shelton et al. |
| 2005/0006429 | A1 | 1/2005 | Wales et al. |
| 2005/0006431 | A1 | 1/2005 | Shelton et al. |
| 2005/0006434 | A1 | 1/2005 | Wales et al. |
| 2005/0067457 | A1 | 3/2005 | Shelton et al. |
| 2005/0067458 | A1 | 3/2005 | Swayze et al. |
| 2005/0085693 | A1 | 4/2005 | Belson et al. |
| 2005/0102017 | A1 | 5/2005 | Mattison |
| 2005/0165415 | A1 | 7/2005 | Wales |
| 2005/0173490 | A1 | 8/2005 | Shelton |
| 2006/0016853 | A1 | 1/2006 | Racenet |
| 2006/0022014 | A1 | 2/2006 | Shelton et al. |
| 2006/0022015 | A1 | 2/2006 | Shelton et al. |
| 2006/0025810 | A1 | 2/2006 | Shelton |
| 2006/0025811 | A1 | 2/2006 | Shelton |
| 2006/0025812 | A1 | 2/2006 | Shelton |
| 2006/0025813 | A1 | 2/2006 | Shelton et al. |
| 2006/0025816 | A1 | 2/2006 | Shelton |
| 2006/0060630 | A1 | 3/2006 | Shelton et al. |
| 2006/0180634 | A1 | 8/2006 | Shelton et al. |
| 2006/0190028 | A1 | 8/2006 | Wales et al. |
| 2007/0084897 | A1 | 4/2007 | Shelton et al. |
| 2007/0102453 | A1 | 5/2007 | Morgan et al. |
| 2007/0170225 | A1 | 7/2007 | Shelton et al. |
| 2010/0181364 | A1 | 7/2010 | Shelton, IV et al. |

FOREIGN PATENT DOCUMENTS

| | | | |
|---|---|---|---|
| DE | 4303544 | A1 | 9/1993 |
| DE | 19534320 | C1 | 2/1997 |
| DE | 19537299 | | 4/1997 |
| DE | 19643073 | | 4/1997 |
| DE | 19647354 | | 5/1998 |
| DE | 1993372 | | 2/2001 |
| EP | 201883 | A2 | 11/1986 |
| EP | 0500353 | A1 | 8/1992 |
| EP | 0674876 | | 4/1995 |
| EP | 0741966 | A2 | 11/1996 |
| EP | 741996 | A2 | 11/1996 |
| EP | 0 832 605 | A | 4/1998 |
| EP | 0832605 | A1 | 4/1998 |
| EP | 1 323 384 | A | 7/2003 |
| EP | 1 522 264 | A | 4/2005 |
| EP | 1522264 | A1 | 4/2005 |
| EP | 1621137 | | 2/2006 |
| EP | 1621141 | | 2/2006 |
| EP | 1621143 | A2 | 2/2006 |
| EP | 1621151 | A2 | 2/2006 |
| EP | 1693008 | A1 | 8/2006 |
| JP | 05-123325 | A | 5/1993 |
| JP | 2002-204801 | A | 7/2002 |
| JP | 2002-314298 | A | 10/2002 |
| JP | 2004-162035 | A | 6/2004 |
| WO | WO 99/02090 | | 1/1999 |
| WO | WO-0078222 | A1 | 12/2000 |
| WO | WO-0156455 | | 8/2001 |
| WO | WO-0162158 | A2 | 8/2001 |
| WO | WO-0162163 | A1 | 8/2001 |
| WO | WO-0228268 | | 4/2002 |
| WO | 03088845 | A2 | 10/2003 |
| WO | 03090630 | A2 | 11/2003 |
| WO | 03094746 | A1 | 11/2003 |
| WO | WO 03/094743 | | 11/2003 |
| WO | WO-03094743 | A1 | 11/2003 |
| WO | 2004014238 | A2 | 2/2004 |
| WO | WO-2004014238 | A2 | 2/2004 |
| WO | 2004/030554 | A1 | 4/2004 |
| WO | WO 2004/050971 | | 6/2004 |
| WO | WO-2004050971 | A2 | 6/2004 |
| WO | 2004086987 | A1 | 10/2004 |

OTHER PUBLICATIONS

Dec. 8, 2008, Office Action for U.S. Appl. No. 11/162,992
Dec. 12, 2008 Office Action for U.S. Appl. No. 11/162,984.
Mar. 10, 2009, Office Action for Mexican Application No. PA/A/2005/008045.
U.S. Appl. No. 11/082,495, filed Mar. 17, 2005, Shelton IV.
European Search Report for 05254681.9, dated May 15, 2009. (3 pages).
European Search Report for 05254700.7, dated May 15, 2009. (3 pages).
European Search Report for 05254699.1, dated May 15, 2009. (3 pages).
Chinese Office Action for Application No. 200610146378.8 dated Jul. 24, 2009.
Chinese Office Action for Application No. 200610144755.4 dated Aug. 7, 2009.
International Search Report for EP App. No. 05254680.1, Jan. 12, 2006.
International Search Report for EP App. No. 05254685.0, Jan. 12, 2006.
International Search Report for EP App. No. 05254694.2, Jan. 12, 2006.
International Search Report for EP App. No. 05254695.9, Jan. 12, 2006.
International Search Report for EP App. No. 06255053.8, Jan. 25, 2007.
Communication for 06 255 058.7.
EPO Search Report dated Feb. 26, 2008 for Application No. 05254700.7.
EPO Search Report dated Feb. 29, 2008 for Application No. 05254681.9.
EPO Search Report dated Mar. 25, 2008 for Application No. 05254703.1.
EPO Search Report dated Mar. 3, 2008 for Application No. 05254699.1.
European Search Report for EP #05254684.3, dated Mar. 27, 2008.
European Search Report for EP 06255057.9, dated Oct. 19, 2007.
European Search Report for EPO Application No. 06255053, dated Jan. 25, 2007.
European Search Report for EPO Application No. 06255057, dated Jan. 29, 2007.
European Search Report for EPO Application No. 06255058, dated Jan. 31, 2007.
European Search Report for EPO Application No. 06255062, dated Nov. 23, 2006.
European Search Report for EPO Application No. 06255064, dated Feb. 9, 2007.
European Search Report for EPO Application No. 06255065, dated Feb. 15, 2007.
Guidelines for Hand and Power Tools http://www.osha.gov/doc/outreachtraining/htmlfiles/tools.html, OSHA, May 1996, p. 3.
Translation of Japanese Office Action for Application No. 2005-217100, Mar. 8, 2011.
Australian Office Action for Application No. 2005203217 dated May 24, 2010.
Australian Office Action for Application No. 2005203222 dated May 12, 2010.
Australian Office Action for Application No. 2006222752 dated Jan. 10, 2012.
Translation of Chinese Office Action for Application No. 200510089519.2 dated May 23, 2008.
Translation of Chinese Office Action for Application No. 200510089529.6 dated Oct. 10, 2008.
Translation of Chinese Office Action for Application No. 200610144753.5 dated Oct. 23, 2009.
EPO Search Report dated Mar. 27, 2008 for Application No. 05254700.7.
EPO Search Report dated Apr. 1, 2008 for Application No. 05254703.1.
EPO Search Report dated Apr. 2, 2008 for Application No. 05254699.1.
European Search Report for EPO Application No. 06255061, dated Nov. 23, 2006.
Translation of Japanese Office Action for Application No. 2005-216963, Jan. 25, 2011.

Translation of Japanese Office Action for Application No. 2005-217069, Mar. 1, 2011.
Translation of Japanese Office Action for Application No. 2005-217080, Mar. 8, 2011.

Translation of Mexican Office Action for Application No. PA/A/2005/008044 dated Feb. 12, 2009.

* cited by examiner

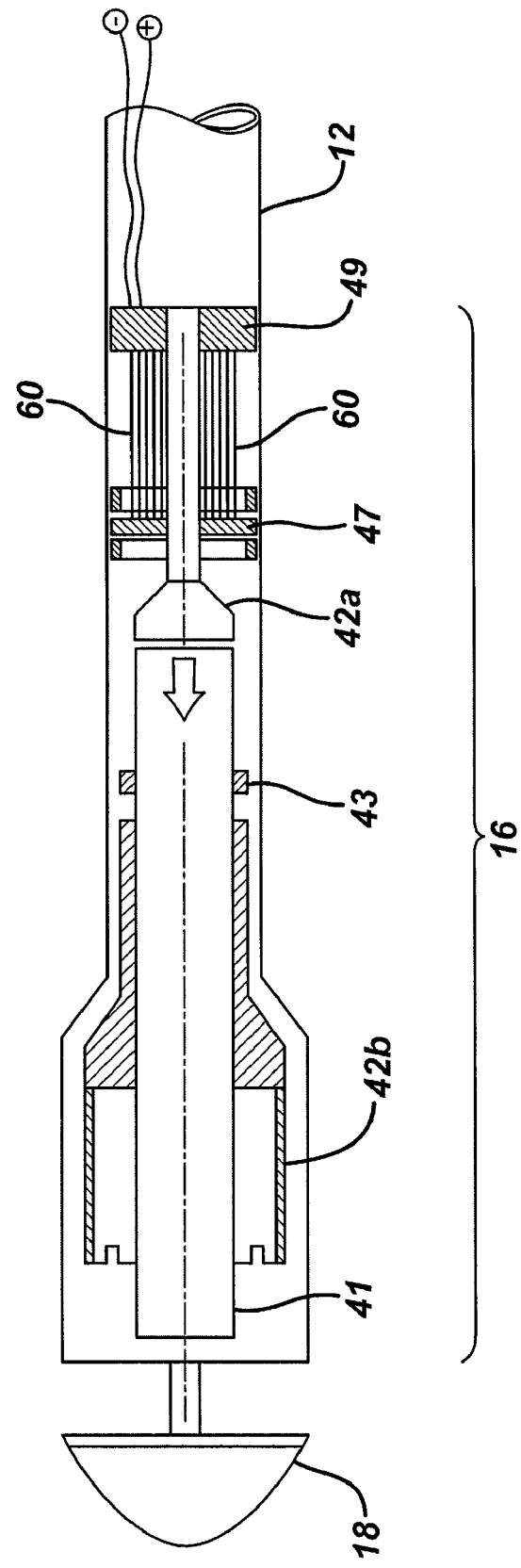

ELECTROACTIVE POLYMER-BASED ARTICULATION MECHANISM FOR CIRCULAR STAPLER

CROSS REFERENCE TO RELATED APPLICATIONS

This application is a continuation-in-part of U.S. patent application Ser. No. 11/082,495 now U.S. Pat. No. 7,506,790 filed on Mar. 17, 2005 and entitled "Surgical Instrument Incorporating an Electrically Actuated Articulation Mechanism," which claims priority to U.S. Provisional Application No. 60/591,694 filed on Jul. 28, 2004 and entitled "Surgical Instrument Incorporating an Electrically Actuated Articulation Mechanism." These applications are hereby incorporated by reference in their entireties.

FIELD OF THE INVENTION

The present invention relates broadly to surgical devices, and in particular to methods and devices for articulating and/or actuating an end effector on a surgical tool, such as a circular stapler.

BACKGROUND OF THE INVENTION

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Anastomosis is the surgical joining of separate tissue sections. Typically, an anastomosis procedure follows surgery in which a diseased or defective section of hollow tissue is removed and the remaining end sections are to be joined, however hemorrhoidal or other tissue can also be anastomized. Depending on the desired anastomosis procedure, the end sections may be joined by either circular, end-to-end, or side-to-side organ reconstruction methods.

In a circular anastomosis procedure, the two ends of the tissue sections are joined by means of a stapling instrument which drives a circular array of staples through each tissue section and simultaneously cores any tissue interior of the driven circular array of staples to create a tubular passage. Known circular staplers typically include an anvil head that is positioned adjacent to a staple holding component. Opposed end portions of the tissue to be stapled are clamped between the anvil head and the staple holding component, and the clamped tissue is stapled by driving one or more staples from the staple holding component so that the ends of the staples pass through the tissue and are deformed by the anvil head. An annular knife can be concurrently or subsequently advanced to core tissue to create a tubular passage.

One drawback to current circular stapling devices is that a large force is required to effect firing, and the force changes throughout the course of the firing stroke. Most current circular stapling devices utilize a hand-squeezed trigger. The load is low during early portions of the stroke when the staples are advancing out of the cartridge and piercing the tissue. Once the staples enter into the anvil pockets, the resistance and load rises rapidly as the staple legs buckle. Then the resistance and load drop down and rise again as the staples are formed. In contrast, the operator has maximum effective strength at the early and mid-stages of the firing stroke, whereas the effective strength is minimized during the final stages of closure. The large force necessary to effect firing, as well as the variations in the force, can often exceed the surgeon's hand strength and could potentially result in binding or other malfunctions that may occur when an unexpectedly higher force is required.

The large force required to effect firing can also interfere with the flexibility or adjustability of the shaft. Currently, the staple holding component can be pivotally coupled to the shaft, or the shaft can be flexible to allow the shaft to travel through a curved pathway. The transfer of force from the handle to the staple holding component can necessarily interfere with the pivoted or curved orientation of the shaft, potentially causing it to straighten.

Accordingly, there remains a need for methods and devices for actuating and/or articulating a circular stapler, and in particular for methods and devices that require a low force to effect actuation and/or articulation of a circular stapler.

BRIEF SUMMARY OF THE INVENTION

The present invention provides various devices and methods for stapling tissue. In one embodiment, a circular stapling device is provided that includes an elongate shaft with a stapling apparatus coupled to the distal end of the elongate shaft and adapted to deliver staples into tissue in a substantially curved pattern. While the stapling apparatus can have a variety of configurations, in one embodiment the stapling apparatus includes a staple applying assembly and an anvil that is coupled to the staple applying assembly and movable between an open tissue-receiving position and a closed staple-applying position. In an exemplary embodiment, the device also includes one or more actuators for effecting articulation and/or actuation of the stapling apparatus. The device can also include a handle that is formed on the proximal end of the elongate shaft and that has a control mechanism for selectively delivering energy to the actuator(s).

In one embodiment, actuation of the device can be achieved using an electroactive polymer actuator that is coupled to the staple applying assembly and that is adapted to drive one or more staples into tissue positioned between the staple applying assembly and the anvil. For example, the staple applying assembly can include a driver that is adapted to move distally to drive staples through the staple applying assembly toward the anvil. The driver can optionally have a blade formed thereon that is adapted to cut stapled tissue. The electroactive polymer actuator can be coupled to the driver and the staple applying assembly, and it can be adapted to move the driver distally when energy is delivered to the electroactive polymer. While the electroactive polymer actuator can have a variety of configurations, in one exemplary embodiment the electroactive polymer actuator can be in the form of one or more electroactive polymer cords that are adapted to axially contract when energy is delivered thereto to pull the driver distally within the staple applying assembly.

In another embodiment, the stapling device can include an electroactive polymer actuator that is coupled to the anvil and that is adapted to move the anvil from the open tissue-receiving position to the closed staple-applying position when energy is delivered to the electroactive polymer actuator. In an exemplary embodiment, the electroactive polymer actuator is in the form of an electroactive polymer cord that axially contracts when energy is delivered thereto to pull the anvil toward the staple applying assembly.

Methods for stapling tissue are also provided. In one embodiment, the method can include inserting a circular stapler into a lumen, positioning tissue to be stapled between an anvil and a staple applying assembly located on a distal end of the circular stapler, and delivering energy to an electroactive polymer actuator coupled to the staple applying assembly to drive a plurality of staples through the staple applying assembly and against the anvil to staple the tissue positioned therebetween with staples positioned in a substantially curved pattern. In one embodiment, delivering energy to the electroactive polymer actuator can be effective to move a driver disposed within the staple applying assembly to drive staples therethrough and against the anvil. In an exemplary embodiment, the electroactive polymer actuator can axially contract when energy is delivered thereto to move the driver through the staple applying assembly. In another embodiment, an electroactive polymer actuator can be coupled to the anvil and energy delivery to the electroactive polymer actuator can pull the anvil toward the staple applying assembly.

In another embodiment, articulation of an end effector of a circular stapling device can be achieved using an electroactive polymer actuator. For example, the device can include an elongate shaft, and an end effector movably coupled to a distal end of the elongate shaft by an articulation joint. The end effector can be adapted to deliver staples into tissue in a substantially curved pattern. The device can also include an electroactive polymer actuator coupled to the articulation joint and adapted to move the end effector about the articulation joint relative to the elongate shaft when energy is delivered to the electroactive polymer actuator.

While various techniques can be used to move the articulation joint using the end effector, in one embodiment the elongate shaft can include a slide bar extending therethrough and having a distal end coupled to the articulation joint. The electroactive polymer actuator can be configured to move the slide bar laterally to effect movement of the end effector. For example, the electroactive polymer actuator can include first and second electroactive polymer actuators disposed on opposed sides of the slide bar. The slide bar can include gears formed on a distal end thereof and adapted to engage corresponding gears formed in the articulation joint. In another embodiment, the articulation joint can be in the form of a pivot joint, and the electroactive polymer actuator can include a first electroactive polymer actuator extending between a first side of the end effector and a first side of the elongate shaft, and a second electroactive polymer actuator extending between a second opposed side of the end effector and a second opposed side of the elongate shaft. In yet another embodiment, the articulation joint can be in the form of a flexible portion formed between the elongate shaft and the end effector. The electroactive polymer actuator can include a plurality of electroactive polymer actuators coupled to the flexible portion at distinct locations, each of the plurality of electroactive polymer actuators being configured to change orientations when energy is selectively delivered thereto to flex the flexible portion.

A method for fastening tissue is also provided and in one embodiment includes inserting an elongate shaft of a circular stapling device into a body lumen to position an end effector movably coupled to a distal end of the elongate shaft adjacent to a surgical site, delivering energy to an electroactive polymer actuator to angularly position the end effector relative to the elongate shaft, and simultaneously advancing a plurality of staples through the end effector to staple tissue disposed adjacent to the end effector. Delivering energy to the electroactive polymer actuator can cause the electroactive polymer actuator to radially expand to move a slide bar, extending through the elongate shaft and coupled to an articulation joint formed between the elongate shaft and the end effector, laterally and thereby effect pivotal movement of the end effector. Alternatively, delivering energy to the electroactive polymer actuator can cause the electroactive polymer actuator to axially contract move a slide bar, extending through the elongate shaft and coupled to an articulation joint formed between the elongate shaft and the end effector, laterally and thereby effect pivotal movement of the end effector. In other embodiments, energy can be delivered to a first electroactive polymer actuator to move the end effector in a first direction, and to a second electroactive polymer actuator to move the end effector in a second, opposed direction. The amount of energy delivered to the electroactive polymer actuator can correspond to a degree of movement of the end effector. In yet another embodiment, delivering energy to an electroactive polymer actuator can angularly position the end effector relative to the elongate shaft by flexing a flexible portion extending between the elongate shaft and the end effector. In other embodiments, prior to simultaneously advancing a plurality of staples, tissue can be engaged between a staple applying assembly and an anvil of the end effector. For example, energy can be delivered to an electroactive polymer actuator to move the anvil toward the staple applying assembly. In yet another aspect, simultaneously advancing a plurality of staples can include delivering energy to an electroactive polymer actuator coupled to a staple advancing to simultaneously advancing a plurality of staples through the end effector to staple tissue disposed adjacent to the end effector.

BRIEF DESCRIPTION OF THE DRAWINGS

The invention will be more fully understood from the following detailed description taken in conjunction with the accompanying drawings, in which:

FIG. 3B is a cross-sectional view of a distal portion of the circular stapler of FIG. 3A showing one exemplary embodiment of an electroactive polymer actuator assembly for actuating the staple applying assembly;

DETAILED DESCRIPTION OF THE INVENTION

Figure 1A:
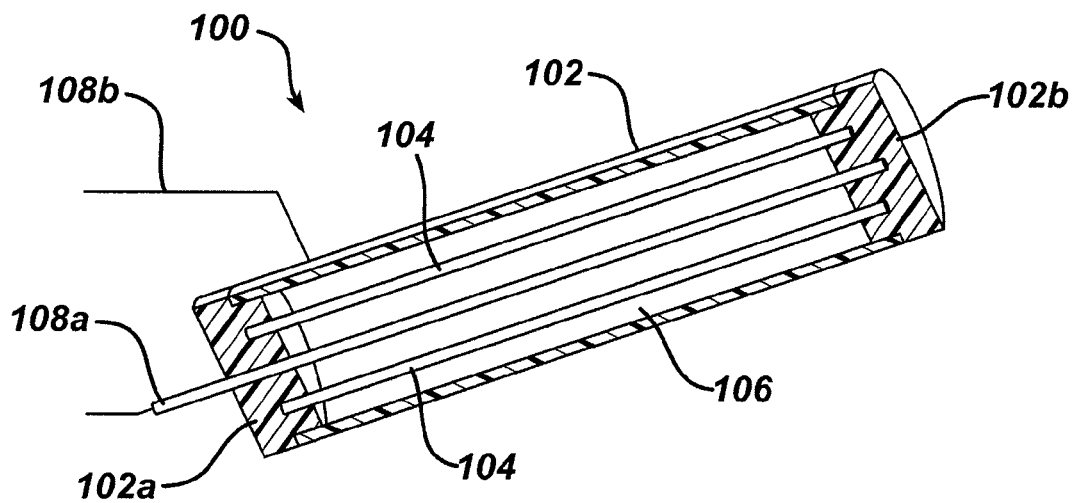
FIG. 1A is a cross-sectional view of a prior art fiber bundle type EAP actuator.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for effecting movement of one or more components of a circular stapler. In one exemplary embodiment, a circular stapler is provided having an elongate shaft with an end effector or staple applying assembly coupled thereto. An electrically expandable and contractible actuator, such as an electroactive polymer actuator, can be used to actuate the staple applying assembly, thereby driving one or more staples, and preferably a plurality of staples in a substantially curved pattern, into tissue. An electrically expandable and contractible actuator can also optionally be used to move an anvil toward a staple applying assembly. In another embodiment, a circular stapler is provided having a stapling apparatus that is movably coupled to a distal end of an elongate shaft. An electrically expandable and contractible motor, such as an electroactive polymer actuator, can be used to pivotally or angularly adjust a position of the stapling apparatus relative to the elongate shaft by delivering energy to the electroactive polymer actuator. A person skilled in the art will appreciate that the circular stapler can have a variety of configurations, and that one or more electroactive polymer actuators can be coupled to one or more components of the circular stapler to effect movement.

Electroactive Polymers

Electroactive polymers (EAPs), also referred to as artificial muscles, are materials that exhibit piezoelectric, pyroelectric, or electrostrictive properties in response to electrical or mechanical fields. In particular, EAPs are a set of conductive doped polymers that change shape when an electrical voltage is applied. The conductive polymer can be paired to some form of ionic fluid or gel and electrodes, and the flow of ions from the fluid/gel into or out of the conductive polymer can induce a shape change of the polymer. Typically, a voltage potential in the range of about 1V to 4 kV can be applied depending on the particular polymer and ionic fluid or gel used. It is important to note that EAPs do not change volume when energized, rather they merely expand in one direction and contract in a transverse direction.

One of the main advantages of EAPs is the possibility to electrically control and fine-tune their behavior and properties. EAPs can be deformed repetitively by applying external voltage across the EAP, and they can quickly recover their original configuration upon reversing the polarity of the applied voltage. Specific polymers can be selected to create different kinds of moving structures, including expanding, linear moving, and bending structures. The EAPs can also be paired to mechanical mechanisms, such as springs or flexible plates, to change the effect that is caused when voltage is applied.

There are two basic types of EAPs and multiple configurations for each type. The first type is a fiber bundle that can consist of numerous fibers bundled together to work in cooperation. The fibers typically have a size of about 30-50 microns. These fibers may be woven into the bundle much like textiles and they are often referred to as EAP yarn. In use, the mechanical configuration of the EAP determines the EAP actuator and its capabilities for motion. For example, the EAP may be formed into long stands and wrapped around a single central electrode. A flexible exterior outer sheath will form the other electrode for the actuator as well as contain the ionic fluid necessary for the function of the device. When voltage is applied thereto, the EAP will swell causing the strands to contract or shorten. The fibers can alternatively be configured to expand or lengthen. An example of a commercially available fiber EAP material is manufactured by Santa Fe Science and Technology and sold as PANION™ fiber and described in U.S. Pat. No. 6,667,825, which is hereby incorporated by reference in its entirety.

Figure 1B:
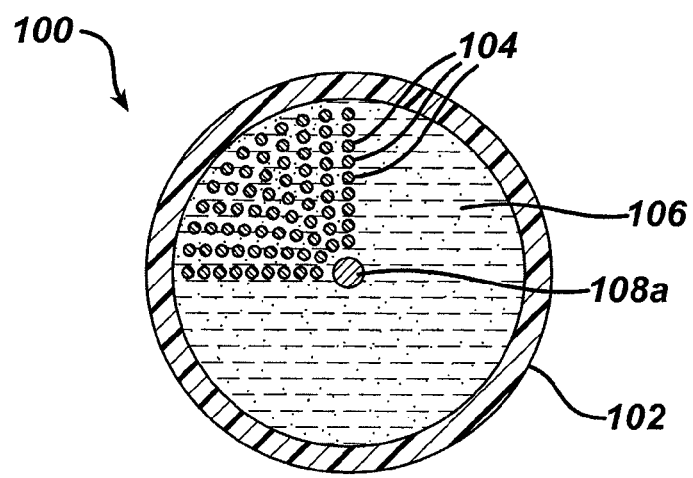
FIG. 1B is a radial cross-sectional view of the prior art actuator shown in FIG. 1A.

FIGS. 1A-1B illustrate one exemplary embodiment of an EAP actuator 100 formed from a fiber bundle. As shown, the actuator 100 generally includes a flexible conductive outer sheath 102 that is in the form of an elongate cylindrical member having opposed end caps 102a, 102b formed thereon. The outer sheath 102 can, however, have a variety of other shapes and sizes depending on the intended use. As is further shown, the outer sheath 102 is coupled to an energy delivering electrode 108a and a return electrode 108b. In the illustrated embodiment, the energy delivering electrode 108a extends through one of the end caps, e.g., end cap 102a, through the inner lumen of the conductive outer sheath 102, and into the opposed end cap, e.g., end cap 102b. The energy delivering electrode 108a can be, for example, a platinum cathode wire, and it can be coupled to any portion of the outer sheath 102. The conductive outer sheath 102 can also include an ionic fluid or gel 106 disposed therein for transferring energy from the energy delivering electrode 108a to the EAP fibers 104, which are disposed within the outer sheath 102. In particular, several EAP fibers 104 are arranged in parallel and extend between and into each end cap 102a, 102b. As noted above, the fibers 104 can be arranged in various orientations to provide a desired outcome, e.g., radial expansion or contraction, or bending movement. In use, energy can be delivered to the actuator 100 through the active energy delivering electrode 106a. The energy will cause the ions in the ionic fluid to enter into the EAP fibers 104, thereby causing the fibers 104 to expand in one direction, e.g., radially such that an outer diameter of each fiber 104 increases, and to contract in a transverse direction, e.g., axially such that a length of the fibers decreases. As a result, the end caps 102a, 102b will be pulled toward one another, thereby contracting and decreasing the length of the flexible outer sheath 102.

The other type of EAP is a laminate structure, which consists of one or more layers of an EAP, a layer of ionic gel or fluid disposed between each layer of EAP, and one or more flexible plates attached to the structure. When a voltage is applied, the laminate structure expands in one direction and contracts in a transverse or perpendicular direction, thereby causing the flexible plate(s) coupled thereto to shorten or lengthen, or to bend or flex, depending on the configuration of the EAP relative to the flexible plate(s). An example of a commercially available laminate EAP material is manufactured by Artificial Muscle Inc, a division of SRI Laboratories. Plate EAP material, referred to as thin film EAP, is also available from EAMEX of Japan.

Figure 2A:
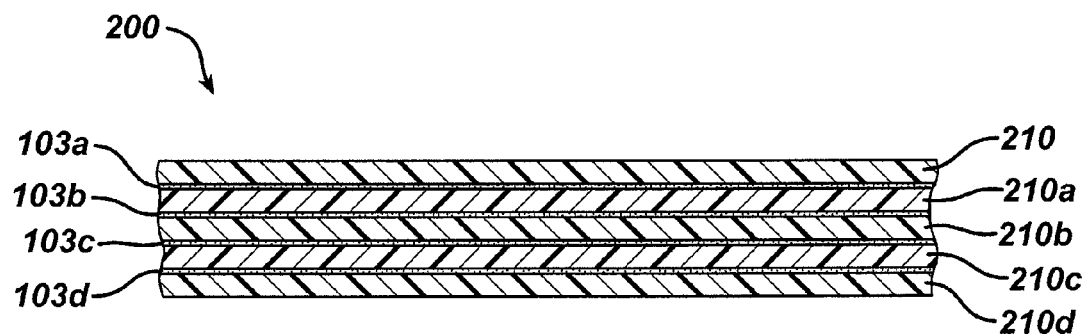
FIG. 2A is a cross-sectional view of a prior art laminate type EAP actuator having multiple EAP composite layers.
Figure 2B:
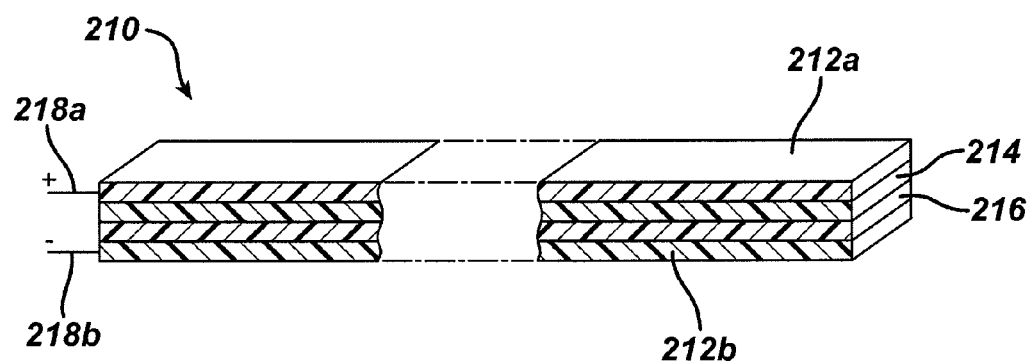
FIG. 2B is a perspective view of one of the composite layers of the prior art actuator shown in FIG. 2A.

FIGS. 2A-2B illustrate an exemplary configuration of an EAP actuator 200 formed from a laminate. Referring first to FIG. 2A, the actuator 200 can include multiple layers, e.g., five layers 210, 210a, 210b, 210c, 210d are shown, of a laminate EAP composite that are affixed to one another by adhesive layers 103a, 103b, 103c, 103d disposed therebetween. One of the layers, i.e., layer 210, is shown in more detail in FIG. 2B, and as shown the layer 210 includes a first flexible conductive plate 212a, an EAP layer 214, an ionic gel layer 216, and a second flexible conductive plate 212b, all of which are attached to one another to form a laminate composite. The composite can also include an energy delivering electrode 218a and a return electrode 218b coupled to the flexible conductive plates 212a, 212b, as further shown in FIG. 2B. In use, energy can be delivered to the actuator 200 through the active energy delivering electrode 218a. The energy will cause the ions in the ionic gel layer 216 to enter into the EAP layer 214, thereby causing the layer 214 to expand in one direction and to contract in a transverse direction. As a result, the flexible plates 212a, 212b will be forced to flex or bend, or to otherwise change shape with the EAP layer 214.

Circular Stapler

Figure 3A:
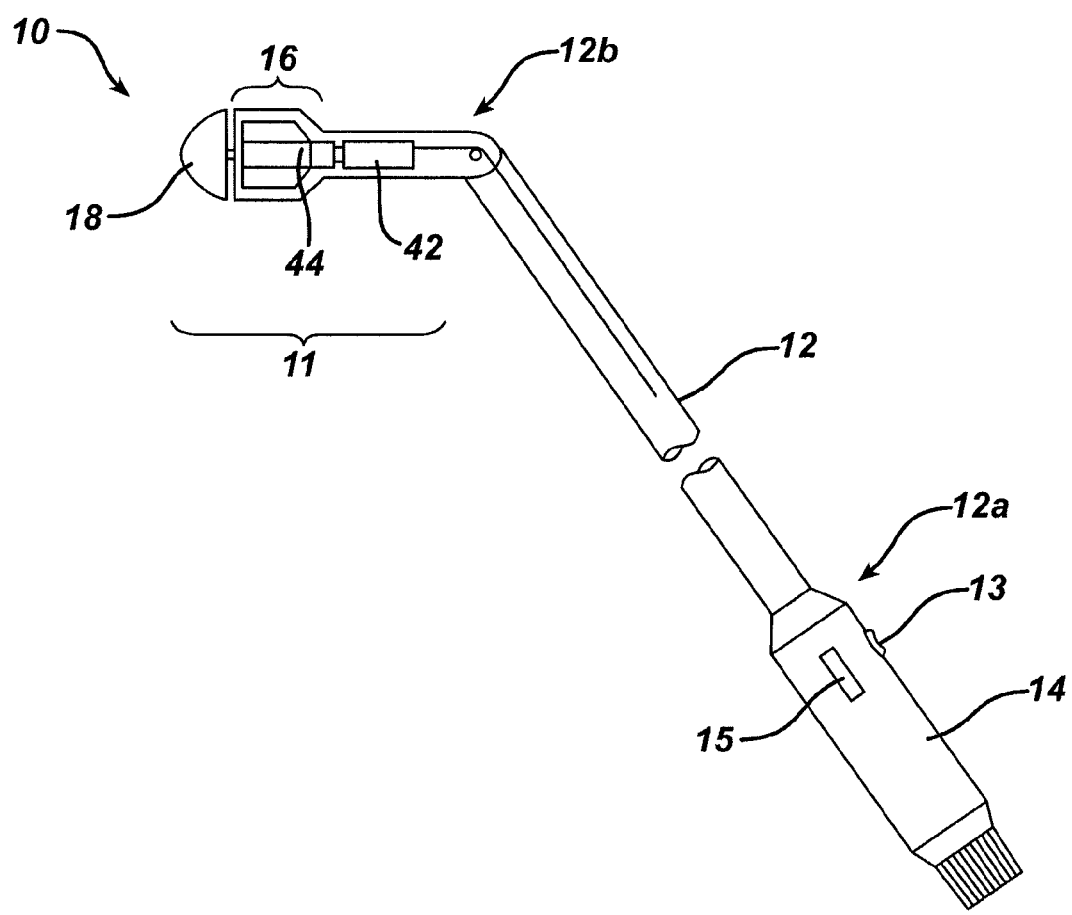
FIG. 3A is a partially cross-sectional perspective view of one exemplary embodiment of a circular stapler having a stapling apparatus formed on a distal end thereof with an anvil and staple applying assembly.
Figure 3C:
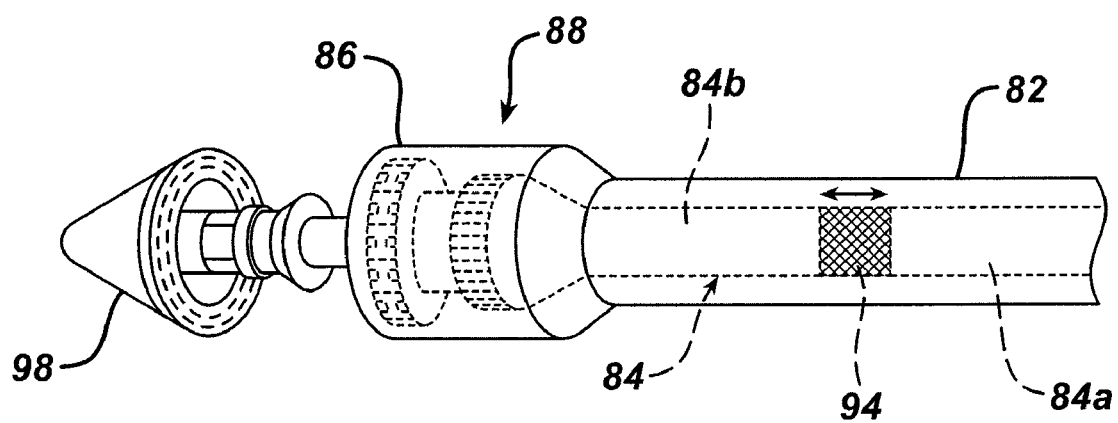
FIG. 3C is a partially cross-sectional view of another embodiment of a distal portion of a circular stapler having an electroactive polymer actuator for driving staples through a staple applying assembly.

As previously indicated, in an exemplary embodiment circular stapling methods and devices are provided that utilize electrically expandable and contractible actuators, such as EAP actuators, to effect articulation and/or actuation of various components of the device. The various methods and devices disclosed herein for effecting articulation and actuation can be incorporated into virtually any circular stapler known in the art, and the circular stapler can include a variety of other features known in the art and not disclosed herein. FIGS. 3A-3C illustrate exemplary circular staplers that can include one or more EAP actuators for effecting articulation and/or actuation. A person skilled in the art will appreciate that, while the various embodiments are described as having EAP actuators for affecting articulation and/or actuation without mechanical assistance, the actuators can alternatively be configured to supplement mechanical articulation and/or actuation.

In general, the stapler 10 includes an elongate shaft 12 having a handle 14 coupled to a proximal end 12a thereof, and a stapling apparatus 11 coupled to the distal end 12b thereof. The stapling apparatus 11 includes a staple applying assembly 16 and an anvil 18 that are adapted to receive tissue therebetween. The staple applying assembly 16 is adapted to contain a staple cartridge 44 having multiple staples disposed therein and configured to be driven into tissue by a plunger or driver 42, and the anvil 18 is adapted to deform the staples. In use, tissue is positioned between the anvil 18 and the staple applying assembly 16, and the anvil 18 is then moved from an open position to a closed position to engage the tissue between the anvil 18 and the staple applying assembly 16. The stapling apparatus 11 can optionally be pivoted relative to the elongate shaft 12 to facilitate positioning of the tissue therein. Once the tissue is engaged between the anvil 18 and the staple applying assembly 16, the staple applying assembly 16 is actuated to drive one or more staples through the tissue and against the anvil 18, which deforms the legs of the staple. In an exemplary embodiment, multiple staples are applied to the tissue in a substantially circular pattern. The circular stapler 10 is particularly suitable for endoscopic and laparoscopic procedures, as the relatively small diameter of the elongate shaft 12 allows it to fit through small access ports or pathways. The stapler, however, can be adapted for use in a variety of medical procedures.

In order to articulate the stapling apparatus (i.e., angularly position the stapling apparatus) relative to the elongate shaft 12, close the anvil 18, and/or actuate (fire) the staple applying assembly 16, the device 10 can include a trigger, rotatable knob, handle, switch, or other mechanism formed on the handle 14. In an exemplary embodiment, as shown in FIG. 3A, the handle 14 includes a first switch 13 formed thereon for closing the stapling apparatus 11, i.e., for moving the anvil 18 toward the staple applying assembly 16. The handle 14 can also include a second switch 15 coupled thereto for firing the staple cartridge 44 in the staple applying assembly 16 to deliver one or more staples or clips into tissue. The second switch 15 can also be effective to advance a blade distally through the staple applying assembly 16 to cut stapled tissue. A person skilled in the art will appreciate that while switches 13, 15 are shown, a trigger, rotatable knob, lever, sliding knob, or other mechanism can be used for articulating the stapling apparatus 11 relative to the elongate shaft 16, moving the anvil 18 toward the staple applying assembly 16, and/or actuating the staple applying assembly 16.

Actuation

As indicated above, the present invention provides exemplary methods and devices for actuating a stapling apparatus on a circular stapler, including firing the staples and optionally driving a knife or blade through the staple applying assembly to cut the stapled tissue. FIG. 3B illustrates a portion of the circular stapler 10 of FIG. 3A in more detail, showing one exemplary embodiment of a technique for firing the staple applying assembly 16 and/or for driving a blade through the staple applying assembly 16 to cut stapled tissue using one or more EAP actuators. A person skilled in the art will appreciate that the stapling apparatus can have a variety of configurations, and that EAP actuators can be incorporated into a variety of other staple applying assemblies to effect firing and/or cutting.

As shown, the elongate shaft 12 includes a plunger 42a disposed therein and adapted to move between a proximal position and a distal position. The plunger 42a can form the staple driver, or it can be coupled to a staple driver 42b, as shown, to advance the staple driver 42b distally, thereby driving staples through the staple applying assembly 16 and toward the anvil 18 and/or to cut tissue engaged by the stapling apparatus 11. As is further shown in FIG. 3B, the plunger 42a is coupled to multiple EAP actuator cords that are effective to move the plunger 42a longitudinally between the proximal and distal positions. In particular, the proximal end of the plunger 42a can include a disc or flange 49 formed therearound, and multiple EAP actuator cords 60 can be coupled to the flange 49 to move the plunger 42a relative to the elongate shaft 12. In the illustrated embodiment, the elongate shaft 12 includes a ground disc 47, which can function as a ground for the EAP actuator cords 60, fixedly coupled to the inner sidewalls thereof. The ground disc 47 is positioned distal of the flange 49 formed on the plunger 42a, and multiple EAP actuator cords 60 extend between the ground disc 47 and the flange 49. When energy is delivered to the EAP actuator cords 60, the cords 60 will axially contract or shorten, thereby pulling the flange 49 and the plunger 42a in a distal direction toward the ground disc 47. As a result, the plunger 42a will advance distally, pushing the staple driver 42b distally to drive staples through the staple cartridge in the staple applying assembly 16. Energy delivery can be terminated to axially expand and return the actuator cords 60 to their initial position, thereby moving the plunger 42a proximally. The plunger 42a can also or alternatively be coupled to a knife driver 43 that is effective to drive a blade 41 distally to cut tissue. In other embodiments, a separate electroactive polymer actuator assembly could be coupled to the knife driver 43 to allow the blade to be driven separate from the staple driver 42b. A person skilled in the art will appreciate that various drivers and/or cutting blades known in the art can be used with the stapling apparatus 11, and that one or more electroactive polymer actuators can be coupled to the driver and/or cutting blade in a variety of configurations to actuate the driver and/or cutting blade.

FIG. 3C illustrates another embodiment of a technique for actuating a staple applying assembly of a circular stapler. In this embodiment, rather than pulling the plunger or driver distally using electroactive polymer actuators that axially contract, the plunger or driver can be pushed axially to drive staples through the staple applying assembly. In particular, FIG. 3C illustrates a distal portion of an elongate shaft 82 of a circular stapler. A driver 84 is slidably disposed within the elongate shaft 82 and it is adapted to move between a proximal position and a distal position, in which the driver 84 drives staples through a staple cartridge 86 disposed within the staple applying assembly 88 and toward an anvil 98, which deforms the staples. An electroactive polymer actuator 94 is disposed between a proximal portion 84a of the driver 84 and distal portion 84b of the driver. This can be achieved, for example, using a laminate or composite type electroactive polymer actuator that is adhered to a terminal end of each of the proximal and distal portions 84a, 84b to connect the portions. In use, energy can be delivered to the electroactive polymer actuator 94 through electrodes that are coupled to a power source that is disposed within the handle of the device or that is mated to the handle of the device. The energy will cause the electroactive polymer actuator to axially expand, thereby pushing the distal portion 84b of the driver 84 toward the staple applying assembly 88 to drive staples through the staple cartridge 86 and toward the anvil 98. Termination of energy delivery will cause the electroactive polymer actuator to axially contract, thereby pulling the distal portion 84b of the driver proximally to its initial position. A person skilled in the art will appreciate that a variety of other techniques can be used to move a driver or plunger of a circular stapler using electroactive polymer actuators.

Articulation

As previously indicated, the present invention also provides exemplary methods and devices for articulating a stapling apparatus of a circular stapler. FIGS. 4A-11B illustrate various exemplary embodiments of articulation joints and electroactive polymer actuators for effecting articulation.

Figure 4A:
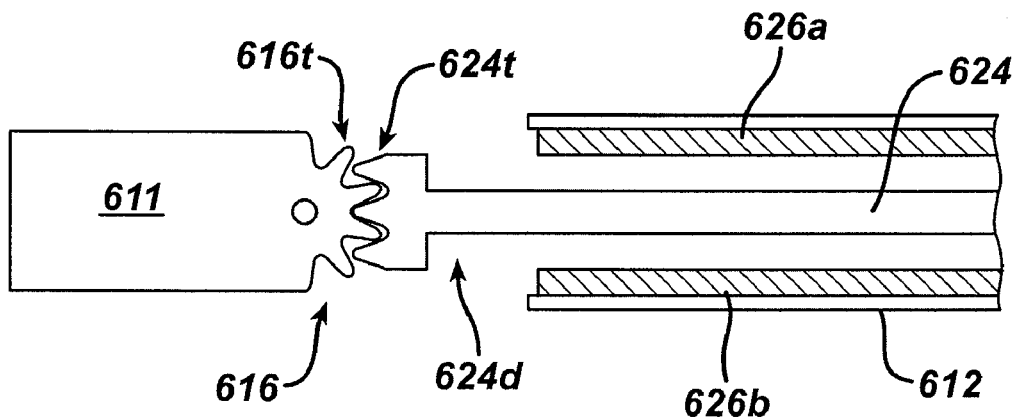
FIG. 4A is a cross-sectional view of a distal portion of an exemplary embodiment of a circular stapler, showing EAP actuators in a non-actuated configuration for effecting articulation of the staple applying assembly.
Figure 4B:
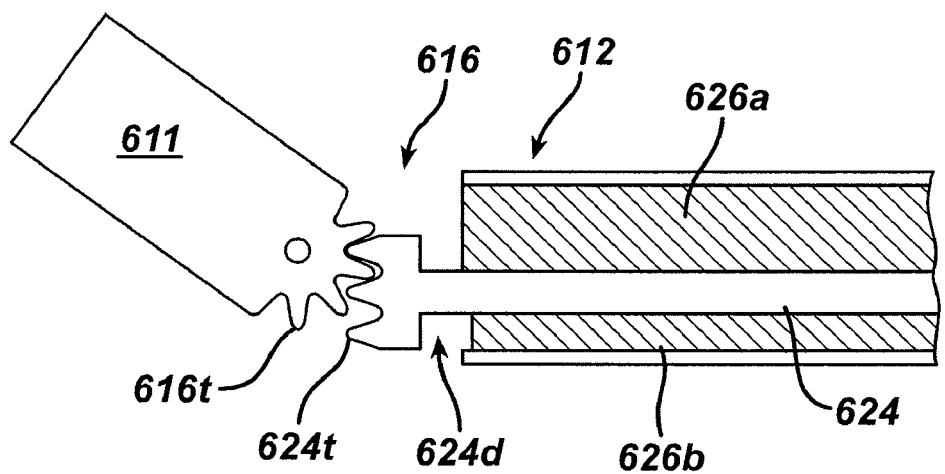
FIG. 4B is a cross-sectional view of the distal portion of the circular stapler shown in FIG. 4A, showing one of the EAP actuators electrically actuated to articulate the staple applying assembly.

Referring first to FIGS. 4A-4B, a distal end 612b of the elongate shaft 612 is shown coupled to a proximal end of the stapling apparatus 611 by a pivot joint 616, such that the stapling apparatus 611 can pivot relative to the shaft 612 about the pivot joint 616. The device also includes a slide bar 624 extending through the elongate shaft 612 and having a distal end 624d with gear teeth 624t formed thereon and adapted to engage corresponding gear teeth 616t formed on the stapling apparatus 611. The device can also include one or more electrically expandable and contractible actuators, such as an EAP actuator, for moving the slide bar 624 to cause the gear teeth 624t on the slide bar 624 to move the gear teeth 624t on the stapling apparatus 611 and thereby pivot the stapling apparatus 611 relative to the elongate shaft 612. While the EAP actuator(s) can effect movement of the slide bar 624 using a variety of techniques, in one exemplary embodiment the EAP actuators are configured to move the slide bar 624 laterally. In particular, a first EAP actuator 626a can extend through at least a portion of the elongate shaft 612 adjacent to a first lateral side of the slide bar 624, and a second EAP actuator 626b can extend through at least a portion of the elongate shaft 612 adjacent to a second, opposed lateral side of the slide bar 624, as shown in FIGS. 4A-4B. Either type of EAP actuator can be used, but in an exemplary embodiment the EAP actuators 626a, 626b are laminate type EAP actuators that are adapted to expand laterally when energy is delivered thereto. FIG. 4A illustrates both actuators 626a, 626b in a non-expanded, un-actuated configuration, where no energy is delivered to either actuator 626a, 626b. FIG. 4B illustrates the first EAP actuator 626a laterally expanded to move the slide bar 624 laterally toward the second EAP actuator 626b, thereby causing the slide bar 624 to pivot the stapling apparatus 611 in a direction opposite to the direction of movement of the slide bar 624. Energy can be delivered to the actuators 626a, 626b through electrodes extending through the shaft 612 and coupled to an energy source disposed within or coupled to a handle of the device, e.g., a battery source or an electrical outlet or other energy source. The handle can also include a control mechanism, such as a sliding lever, rotatable knob, or dial, coupled thereto and adapted to control the amount of energy delivered to each actuator 626a, 626b. The amount of energy delivered to each actuator 626a, 626b is determinative of the amount of expansion of the actuators 626a, 626b, thus allowing the amount of pivotal movement of the stapling apparatus 611 to be selectively adjusted.

A person skilled in the art will appreciate that, while FIGS. 4A-4B illustrate a laterally-moving slide bar 624 with laterally expanding EAP actuators 626a, 626b, the slide bar 624 and actuators 626a, 626b can have a variety of other configurations. For example, multiple EAP actuators in the form fiber bundles can extend laterally between an inner surface of the elongate shaft 612 and the slide bar 624. When energy is delivered to the actuators, the actuators can contract or shorten in length to pull the slide bar 624 toward the elongate shaft 612, thereby moving the slide bar 624 laterally. Alternatively, the slide bar 624 can be configured to move longitudinally to effect movement of the stapling apparatus 611, and the EAP actuator can be used to effect longitudinal movement of the slide bar 624. In other embodiments, the slide bar itself, or at least a portion of the slide bar, can be formed from an EAP actuator that is adapted to expand axially in a desired direction to move the slide bar laterally.

Figure 5A:
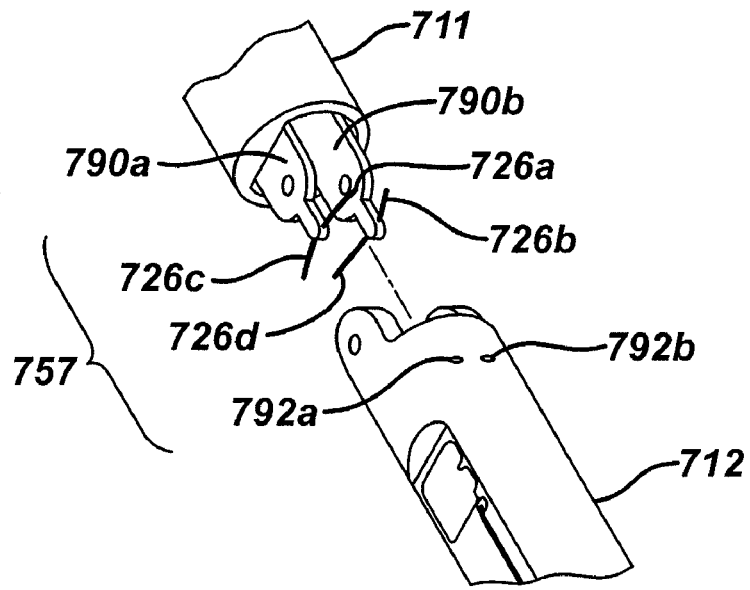
FIG. 5A is an exploded perspective view of another embodiment of a staple applying assembly movably coupled to a distal portion of an elongate shaft and having EAP actuators for articulating the staple applying assembly.
Figure 5B:
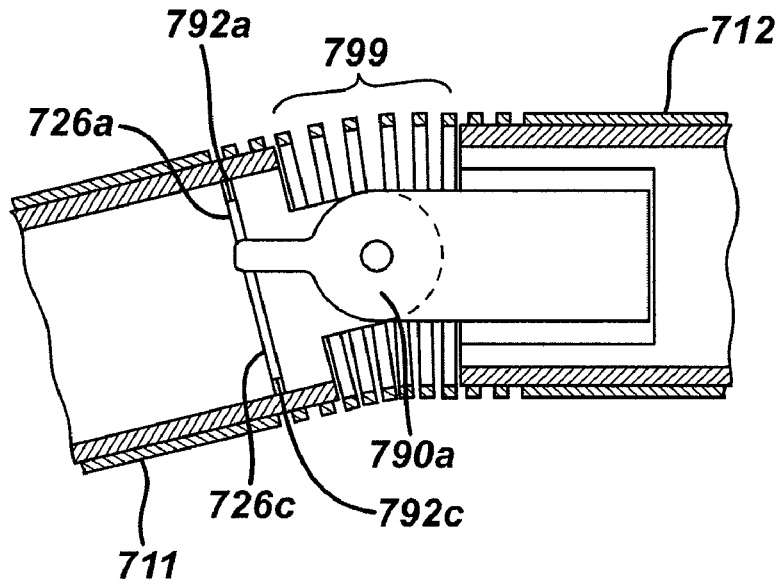
FIG. 5B is a partially cross-sectional view of the staple applying assembly and elongate shaft shown in FIG. 5A, showing one of the EAP actuators electrically actuated to articulate the staple applying assembly.

FIGS. 5A-5B illustrate another embodiment of a technique for articulating a circular stapler. In this embodiment, the stapling apparatus 711 is pivotally coupled to the elongate shaft 712 by first and second opposed arms 790a, 790b coupled to opposed sides of the elongate shaft 712. First and third EAP actuators 726a, 726c are attached to and extend from opposed sides of a terminal end of the first arm 790a, and second and fourth EAP actuators 726b, 726d are attached to and extend from opposed sides of a terminal end of the second arm 790b. The distal end of each EAP actuator 726a-d is coupled to an inner sidewall of the elongate shaft 712 at an attachment point (first, second, and third attachment points 792a, 792b, 792c are shown). As a result, the first and second actuators 726a and 726b are attached to one side of the elongate shaft 712, and the third and fourth actuators 726c and 726d are attached to an opposite side of the elongate shaft 712. In use, energy can be delivered to the first and second EAP actuators 726a, 726b to cause the actuators 726a, 726b to axially contract or shorten, thereby pulling the first and second arms 790a, 790b in a lateral direction towards the first and second attachment points 792a, 792b. As a result, the stapling apparatus 711 is pivoted in a first direction. When energy delivery is terminated, the first and second actuators 726a, 726b will axially expand returning to their initial configuration, thereby moving the stapling apparatus 711 to its initial position in which it is longitudinally aligned with the elongate shaft 712. Energy can be delivered to the third and fourth actuators 726c, 726d to similarly move the stapling apparatus 711 in an opposite direction. As previously discussed, the amount of energy delivered can be controlled to control the amount of pivotal movement of the stapling apparatus 711. As shown in FIG. 5B, the device can also include a covering 799 surrounding at least a portion of the pivot frame assembly 757 to provide support thereto.

Figure 6:
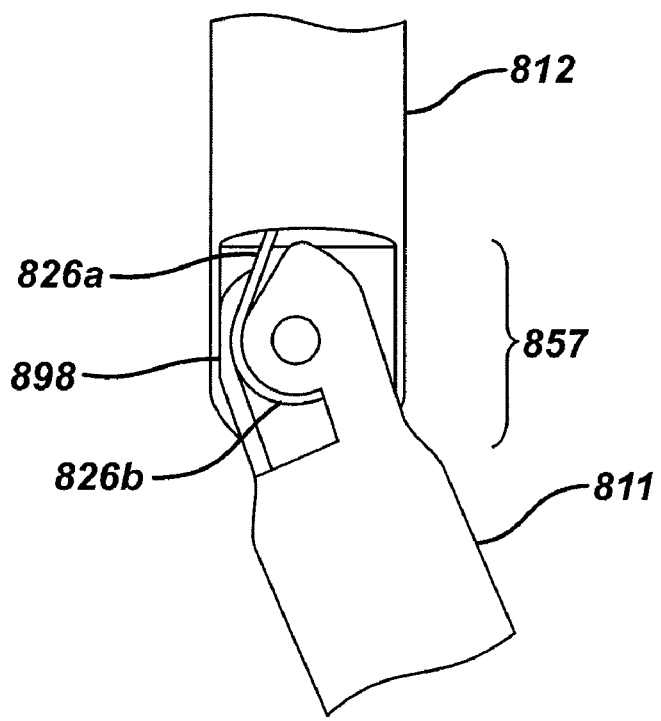
FIG. 6 is a partially cross-sectional view of another embodiment of a staple applying assembly movably coupled to a distal portion of an elongate shaft and having EAP actuators for articulating the staple applying assembly.

FIG. 6 illustrates yet another embodiment of a technique for articulating a circular stapler. In this embodiment, one or more actuating members can be incorporated into a pulley 898 that is part of a pivoting frame assembly 857. The pulley 898 can be made entirely of EAP actuators or, alternatively, EAP actuators can be attached to proximal and distal ends of the pulley 898. In the illustrated embodiment, first and second EAP actuators 826a, 826b are attached to the proximal and distal ends of the pulley 898. The EAP actuators 826a, 826b are anchored to the elongate shaft 812 to push and pull the stapling apparatus 811 to effect articulation. In particular, energy delivery to one of the EAP actuators, e.g., the first EAP actuator 826a, causes the first EAP actuator 826a to axially contract or shorten to move the pulley 898 in a first direction, thereby causing the stapling apparatus 811 to pivot in a first direction. Conversely, energy delivery to the second EAP actuator 826b causes the second EAP actuator to axially contract or shorten to move the pulley 898 in a second, opposite direction, thereby causing the stapling apparatus 811 to pivot in a second, opposite direction. Again, energy delivery can be controlled to control the amount of movement of the stapling apparatus 811.

Figure 7A:
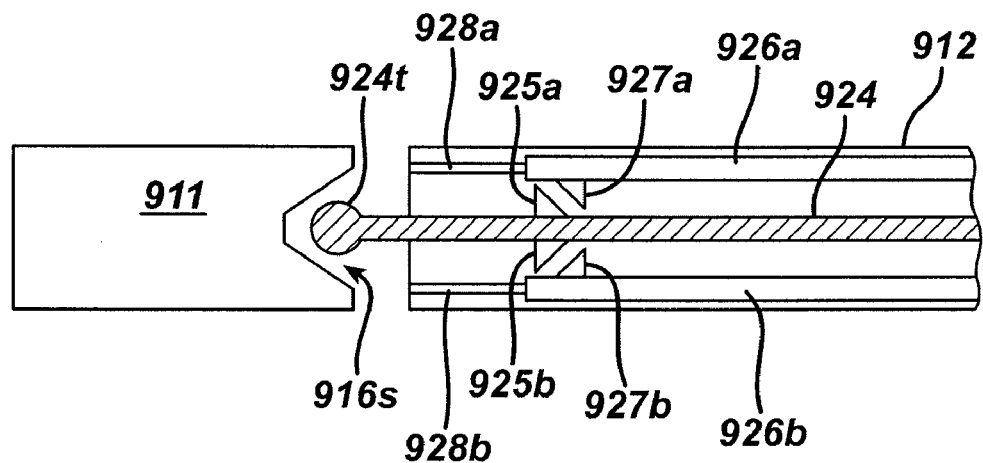
FIG. 7A is a partially cross-sectional view of another embodiment of a staple applying assembly movably coupled to a distal portion of an elongate shaft and having EAP actuators for articulating the staple applying assembly.
Figure 7B:
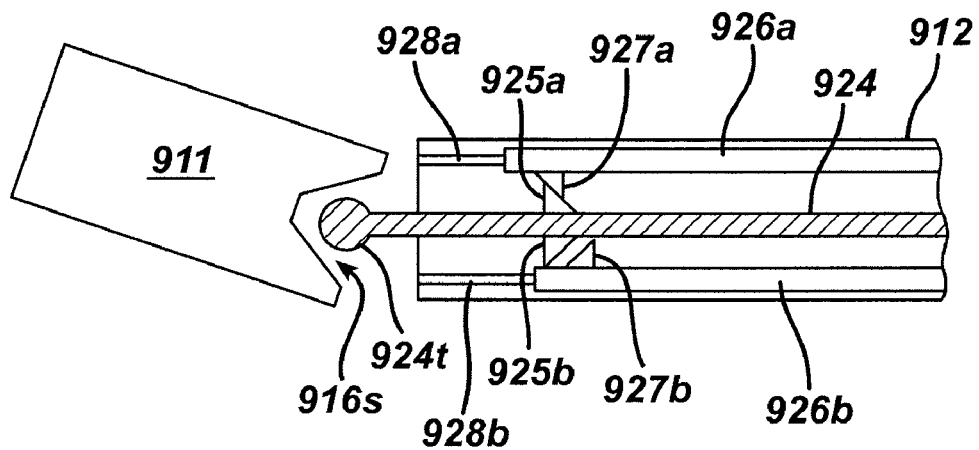
FIG. 7B is a partially cross-sectional view of the staple applying assembly and elongate shaft shown in FIG. 7A, showing one of the EAP actuators electrically actuated to articulate the staple applying assembly.

FIGS. 7A-7B illustrate another embodiment of a technique for articulating a stapling apparatus relative to an elongate shaft of a circular stapler. In this embodiment, the elongate shaft 912 includes a slide bar 924 extending therethrough and having a ball 924t formed on a distal end thereof and received within a corresponding socket 916s formed in a proximal end of the stapling apparatus 911. The slide bar 924 also includes cam surfaces 925a, 925b formed thereon, preferably at a location proximal to the distal end of the elongate shaft 912. The cam surfaces 925a, 925b can have a variety of shapes and sizes, but in an exemplary embodiment, as shown, the cam surfaces 925a, 925b extend outward from opposed sides of the slide bar 924 and they are wedge-shaped members that increase in width in a proximal-to-distal direction. The device also includes first and second actuating members 926a, 926b extending through the elongate shaft 912 and positioned on opposed sides of the slide bar 924. Each actuating member 926a, 926b includes a cam surface 927a, 927b formed thereon and adapted to abut against the cam surfaces 925a, 925b formed on the slide bar 924. As a result, distal movement of the first actuating member 926a will cause the cam surface 927a formed thereon to slide against the cam surface 925a formed on the slide bar 924, thereby moving the slide bar 924 laterally away from the first actuating member 926a. As a result of the lateral movement of the slide bar 924, the ball 924t will cause the stapling apparatus 911 to pivot relative to the elongate shaft 912. Conversely, distal movement of the second actuating member 926b will cause the cam surface 927b formed thereon to slide against the cam surface 925b formed on the slide bar 924, thereby moving the slide bar 924 laterally away from the second actuating member 926b, and thus pivoting the stapling apparatus 911 in an opposite direction. A biasing element (not shown), such as a spring, can be disposed on each side of the slide bar 924 to bias the slide bar 924 to the central, resting position shown in FIG. 7A, thereby allowing the slide bar 924 to return to the resting position when the actuating member 926a, 926b is moving proximally.

In an exemplary embodiment, movement of each actuating member 926a, 926b can be achieved using an EAP actuator coupled thereto. As shown in FIGS. 7A-7B, an EAP actuator cord 928a, 928b, preferably in the form of a fiber bundle type actuator, extends between a distal end of each actuating member 926a, 926b and a distal end of the shaft 912. When energy is selectively delivered to one of the EAP actuating cords, e.g., the first actuating cord 928a, the cord 928a will axially contract or shorten, as shown in FIG. 7B, thereby pulling the actuating member 926a coupled to the actuated EAP cord 928a in a distal direction. The cam surface 927a on the actuating member 926a will abut against the cam surface 925a on the slide bar 924 to move the slide bar 924 laterally toward the second actuating member 926b. As a result, the ball 924t on the distal end of the slide bar 924 will cause the stapling apparatus 911 to articulate or pivot thereabout.

A person skilled in the art will appreciate that the EAP actuators can have a variety of other configurations, and they can effect movement of the slide bar using a variety of other techniques. For example, rather than pulling the slide bar 924 distally when energy is delivered to the EAP actuating cords 928a, 928b, the EAP actuators can be coupled to a proximal end of the slide bar 924 and they can be adapted to push the slide bar 924 distally. In other embodiments, the cam surface 927a, 927b formed on each actuating member 926a, 926b can be formed from an EAP actuator such that energy delivery to the cam surface 927a, 927b causes the cam surface 927a, 927b to expand toward the slide bar 924, thereby moving the slide bar 924 in a desired direction to articulate the stapling apparatus 911. The amount of movement of each actuating member 926a, 926b, and thus the amount of articulation of the stapling apparatus 911, can also be controlled by controlling the amount of energy delivered to each EAP actuator.

Figure 8A:
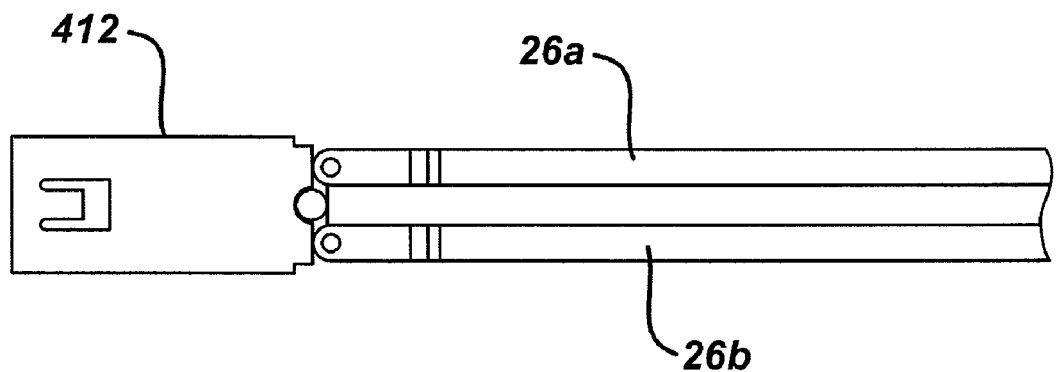
FIG. 8A is a partially cross-sectional view of yet another embodiment of a staple applying assembly movably coupled to a distal portion of an elongate shaft and having EAP actuators for articulating the staple applying assembly.
Figure 8B:
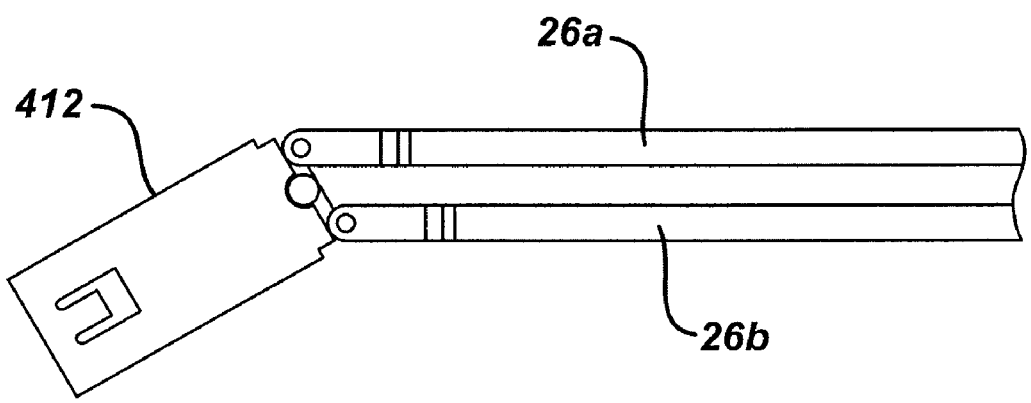
FIG. 8B is a partially cross-sectional view of the staple applying assembly and elongate shaft shown in FIG. 8A, showing one of the EAP actuators electrically actuated to articulate the staple applying assembly.

FIGS. 8A-8B illustrate yet another embodiment of a technique for articulating a stapling apparatus of a circular stapler. In this embodiment, rather than using a slide bar to pivot the stapling apparatus, two actuating members 26a, 26b are coupled directly to opposed sides of the stapling apparatus 412 to push and pull the stapling apparatus 412 to effect articulation. In particular, a distal end of each actuating member 26a, 26b is coupled to a proximal end of the stapling apparatus 412 by a pivot joint, such that proximal movement of the first actuating member 26a causes the stapling apparatus 412 to pivot about the second actuating member 26b, and proximal movement of the second actuating member 26b causes the stapling apparatus 412 to pivot about the first actuating member 26a. The actuating members 26a, 26b can be moved using a variety of techniques. For example, all or a portion of each actuating member 26a, 26b can be formed from an EAP that is adapted to axially expand, or the actuating members 26a, 26b can be coupled to an EAP actuator for moving the actuating members 26a, 26b proximally and distally to articulate the stapling apparatus 412.

Figure 9:
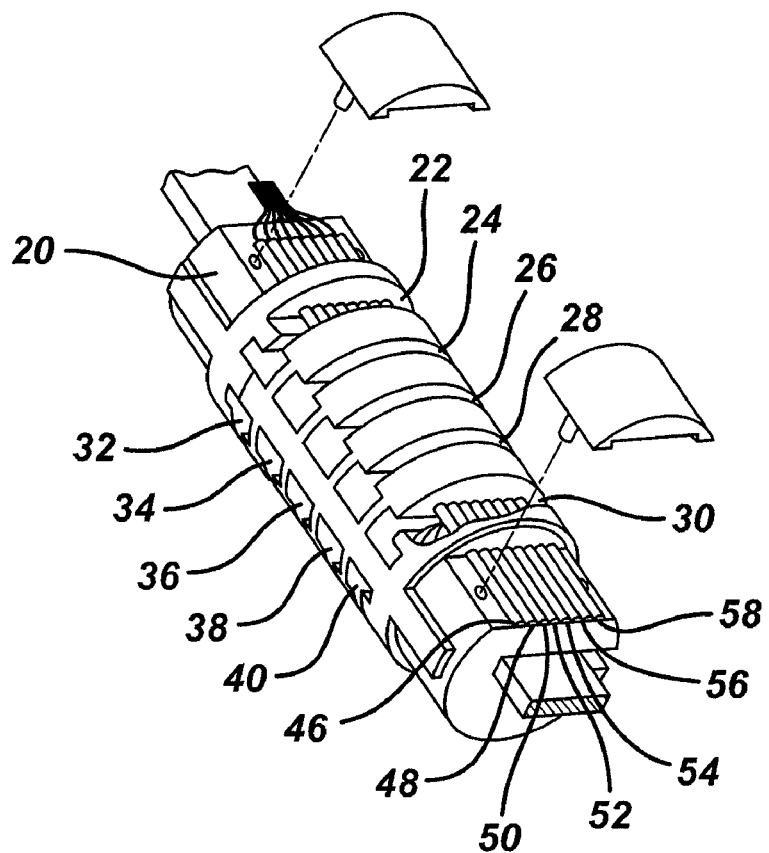
FIG. 9 is a perspective view of yet another embodiment of a staple applying assembly movably coupled by a flexible portion to a distal portion of an elongate shaft and having EAP actuators for articulating the staple applying assembly.

FIG. 9 illustrates another embodiment of a technique for articulating a stapling apparatus of a circular stapler. In this embodiment, the elongate shaft 20 includes a flexible portion formed by a plurality of cut out portions 22, 24, 26, 28, 30, 32, 34, 36, 38, 40 (hereinafter 22-40) formed on opposed sides of the elongate shaft 20. The cut out portions allow the elongate shaft 20 to flex thereabout. One or more actuators can be positioned relative to the cut out portions to effect pivotal or bending movement of a stapling apparatus (not shown) relative to the elongate shaft 20. FIG. 9 illustrates multiple EAP actuator cords 46, 48, 50, 52, 54, 56, 58 (hereinafter 46-58) extending longitudinally through the elongate shaft 20 where the cut out portions are formed. The EAP actuator cords 46-58 extend longitudinally parallel to one another, and they are coupled to the elongate shaft 20 at a first end just proximal to the cut out portions 22-40 and at a second end just distal to the cut out portions 22-40. In use, energy can be selectively delivered to any one or combination of the EAP actuator cords 46-58 to flex the cut out portions 22-40 and thereby articulate the stapling apparatus in a desired direction. For example, energy can be delivered to the first EAP actuator cord 46 to cause the first actuator cord 46 to axially contract or shorten, thereby pulling the opposed ends of the cord 46 toward one another. Since the ends of the first actuator cord 46 are attached to the elongate shaft 20 at opposed ends of the cut out portions, and since the first EAP actuator cord 46 is offset from a central axis of the elongate shaft 20, the first EAP actuator cord 46 will cause the elongate shaft 20 to bend in a first direction. Accordingly, one or more actuator cords 46-58 can be selectively activated, i.e., energy can be selectively delivered thereto, to effect movement of the stapling apparatus in a desired direction. A person skilled in the art will appreciate that a variety of other techniques can be used to cause the cut out portions to bend.

Figure 10:
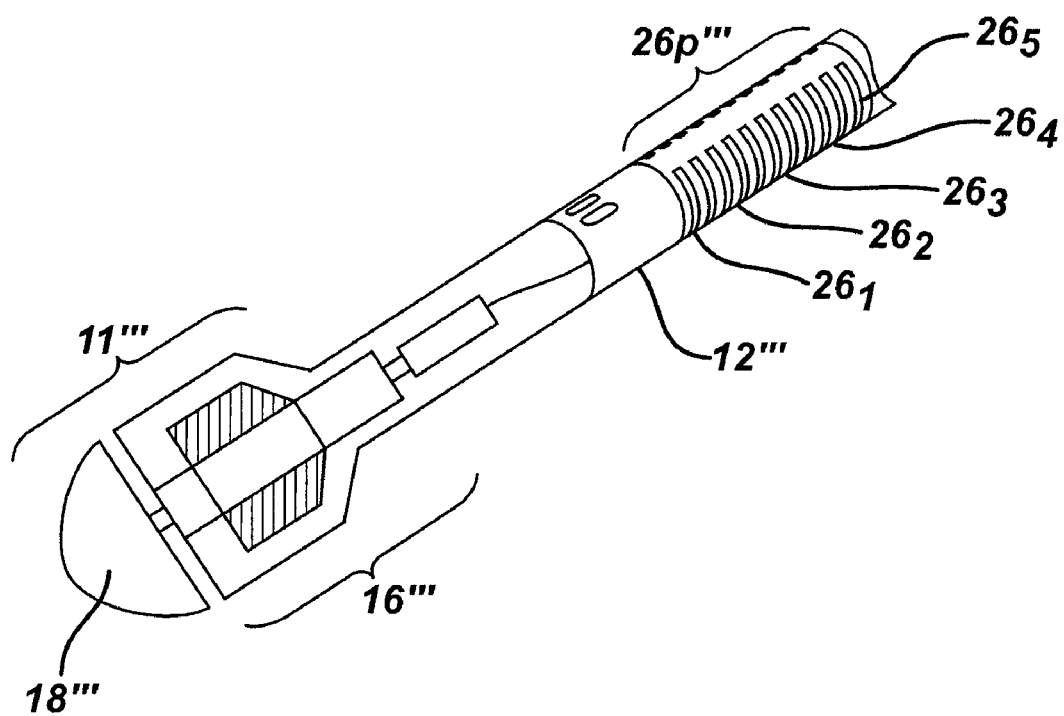
FIG. 10 is a perspective view of yet another embodiment of a staple applying assembly movably coupled by a flexible portion to a distal portion of an elongate shaft and having EAP actuators for articulating the staple applying assembly.

FIG. 10 illustrates yet another embodiment of a technique for articulating a stapling apparatus using a flexible portion 12p''' formed between the stapling apparatus and the elongate shaft 12'''. In this embodiment, one or more EAP actuators can be positioned within, on, or around the flexible portion 12p''' of the elongate shaft 12''' at various locations, and the EAP actuators can be configured to flex the flexible portion 12p''' when energy is delivered to the actuators, thereby articulating the stapling apparatus. FIG. 10 illustrates multiple EAP actuators $26_1, 26_2, 26_3, 26_4, 26_5$ extending axially along distinct portions of the flexible portion 12p''' of the elongate shaft 12'''. While not shown, multiple EAP actuators can be positioned at various other locations around the circumference of the flexible portion 12p'''. In use, energy delivery to the first actuator $26_1$, for example, can cause the first actuator $26_1$ to axially contract thereby bending a portion of the flexible portion 12p'''. A user can thus selectively deliver energy to one or more actuators to articulate and position the stapling apparatus as desired.

A person skilled in the art will appreciate that any of the above embodiments can include a locking feature that allows the device to maintain its articulated position when energy delivery is terminated to the EAP actuators. In particular, when energy delivery is terminated the EAP actuator(s) axially expands to return the stapling apparatus to its initial position in which it is longitudinally aligned with the elongate shaft. A locking mechanism can thus be used to lock the stapling apparatus in a desired articulated position prior to terminating energy delivery to the EAP actuators.

Figure 11A:
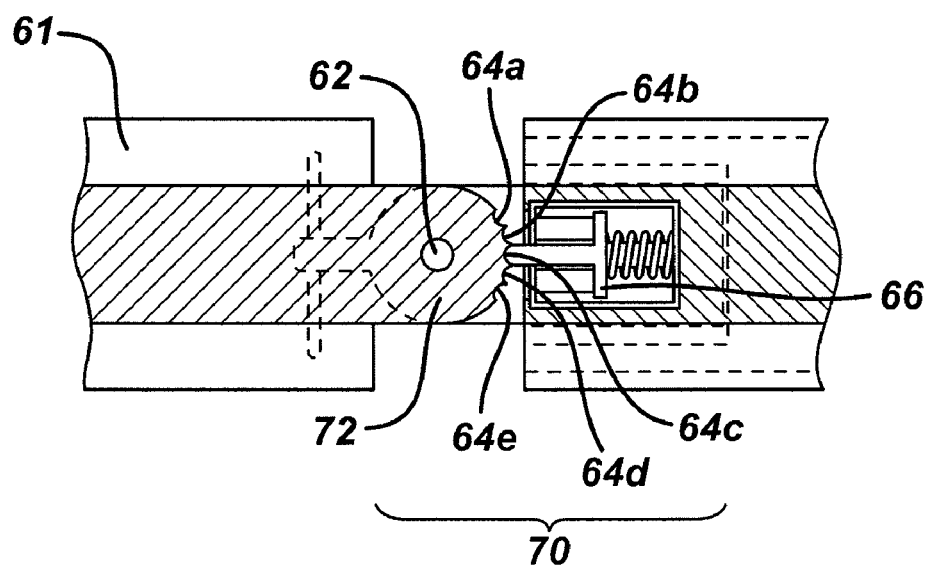
FIG. 11A is a perspective view of one exemplary embodiment of a locking mechanism in an unactivated position for locking a movable joint between a staple applying assembly and an elongate shaft in any of FIGS. 4A-10.
Figure 11B:
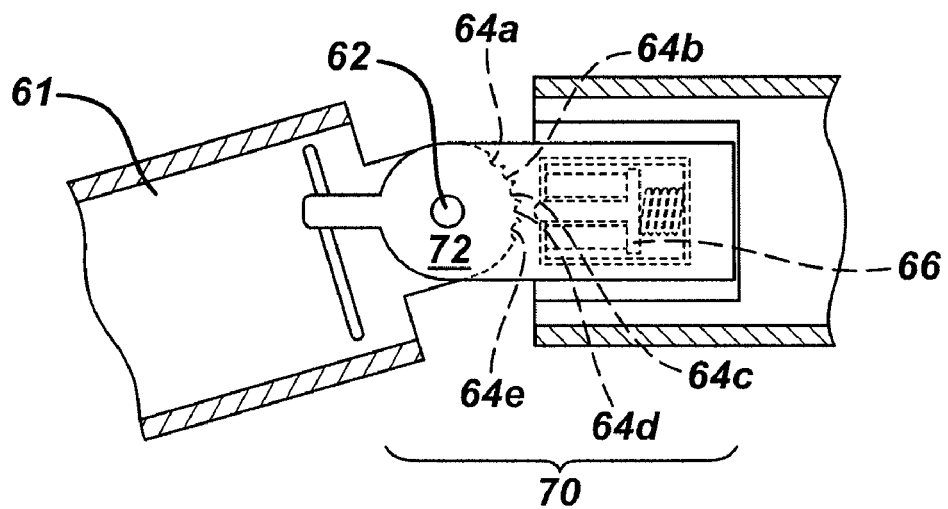
FIG. 11B is a perspective view of the locking mechanism of FIG. 11A activated to lock the movable joint in a fixed position.

While the locking mechanism can have a variety of configurations, FIGS. 11A-11B illustrate one exemplary embodiment of an articulation lock 70 that is incorporated into a pivoting articulation joint 62. As shown, the articulation joint 62 includes a rotary structure 72 having a plurality of holes 64a, 64b, 64c, 64d, 64e that are adapted to receive a plunger to prevent rotational movement of the articulation joint 62. A stop, which in one embodiment can be a spring loaded plunger 66, is formed within the elongate shaft 61 of the device and located proximal to the rotary structure 72. The plunger 66 is also coupled to an EAP actuator (not shown) that, when actuated with energy, effects movement of the plunger 66 thereby allowing the articulation joint 62 to move. In particular, as shown in FIG. 11A, when the device is in an un-actuated position, the plunger 66 rests in one of the holes (hole 64e as shown) of the rotary structure 72, thereby maintaining the stapling apparatus in a fixed position. Energy delivery to the EAP actuator, as shown in FIG. 11B, will pull the plunger 66 out of the hole 64e to allow the articulation joint 62 to move to a desired position. The various techniques previously described can be used to articulate the stapling apparatus. Once the stapling apparatus is moved to a desired articulated position, the EAP actuator can be de-actuated, i.e., energy delivery can be terminated, allowing the spring to bias the plunger 66 into one of the holes of the rotary structure 72. The stapling apparatus is thereby again maintained in a fixed position. One skilled in the art will appreciate that a variety of other locking mechanisms can be incorporated into an articulating joint, such as a ratchet and teeth system.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A circular stapling device, comprising:
    an elongate shaft;
    an end effector movably coupled to a distal end of the elongate shaft by an articulation joint, the end effector being adapted to deliver staples into tissue in a substantially curved pattern; and
    an electroactive polymer actuator coupled to the articulation joint and adapted to move the end effector about the articulation joint relative to the elongate shaft when energy is delivered to the electroactive polymer actuator, wherein the elongate shaft includes a slide bar extending therethrough and having a distal end coupled to the articulation joint, the electroactive polymer actuator being configured to move the slide bar laterally to effect movement of the end effector.

2. The device of claim 1, further comprising a staple advancing assembly disposed through the elongate shaft and adapted to simultaneously advance a plurality of staples in a substantially circular pattern through the end effector.

3. The device of claim 1, wherein the electroactive polymer actuator comprises first and second electroactive polymer actuators disposed on opposed sides of the slide bar.

4. The device of claim 1, wherein the slide bar includes gears formed on a distal end thereof and adapted to engage corresponding gears formed in the articulation joint.

5. The device of claim 1, wherein the articulation joint comprises a pivot joint, and the electroactive polymer actuator comprises a first electroactive polymer actuator extending between a first side of the end effector and a first side of the elongate shaft, and a second electroactive polymer actuator extending between a second opposed side of the end effector and a second opposed side of the elongate shaft.

6. The device of claim 1, wherein the articulation joint comprises a flexible portion formed between the elongate shaft and the end effector.

7. The device of claim 6, wherein the electroactive polymer actuator comprises a plurality of electroactive polymer actuators coupled to the flexible portion at distinct locations, each of the plurality of electroactive polymer actuators being configured to change orientations when energy is selectively delivered thereto to flex the flexible portion.

* * * * *